United States Patent
Hamamah et al.

(10) Patent No.: US 11,230,736 B2
(45) Date of Patent: Jan. 25, 2022

(54) METHODS FOR ASSESSING PREGNANCY OUTCOME

(71) Applicants: INSERM (Institut National de la Santé et de la Recherche Médicale), Paris (FR); Université de Montpellier, Montpellier (FR); Centre Hospitalier Universitaire de Montpellier, Montpellier (FR)

(72) Inventors: Samir Hamamah, Montpellier (FR); Delphine Haouzi, Montpellier (FR)

(73) Assignees: INSERM (Institut National de la Santé de la Recherche Médicale), Paris (FR); Université de Montpellier, Montpellier (FR); Centre Hospitalier Universitaire de Montpellier, Montpellier (FR)

( * ) Notice: Subject to any disclaimer, the term of this patent is extended or adjusted under 35 U.S.C. 154(b) by 139 days.

(21) Appl. No.: 16/498,883

(22) PCT Filed: Mar. 28, 2018

(86) PCT No.: PCT/EP2018/057959
§ 371 (c)(1),
(2) Date: Sep. 27, 2019

(87) PCT Pub. No.: WO2018/178171
PCT Pub. Date: Oct. 4, 2018

(65) Prior Publication Data
US 2020/0040395 A1 Feb. 6, 2020

(30) Foreign Application Priority Data

Mar. 29, 2017 (EP) .................................... 17305362

(51) Int. Cl.
*C12Q 1/6883* (2018.01)
(52) U.S. Cl.
CPC ..... *C12Q 1/6883* (2013.01); *C12Q 2600/178* (2013.01)
(58) Field of Classification Search
None
See application file for complete search history.

(56) References Cited

FOREIGN PATENT DOCUMENTS

WO 2014/062442 A1 4/2014

OTHER PUBLICATIONS

Rekker (Genes 2018 vol. 9 No. 574 pp. 1-17).*
Ghorai (Frontiers in Genetics Apr. 2014 vol. 5 article 100).*
Sha et al.; "Genome-wide identifcation of micro-ribonucleic acids associated with human endometrial receptivity in natural and stimulated cycles by deep sequencing"; Fertility and Sterility, vol. 96, No. 1, Jul. 1, 2011, pp. 150-155.
Kinhal et al.; "Identification of exosomal miRNA biomarkers at early gestation (<18 weeks) in asymptomatic women at early gestation (<18 weeks) who subsequently develop spontaneous preterm birth"; Placenta, vol. 45, 2016, p. 125.
Moussaddykine et al.; "MicroRNAs: novel potentiol of cumulus cells biomarkers to predict embryo's pregnancy outcome"; Human Reproduction, vol. 26, No. Suppl. 1, Jul. 6, 2011, pp. 186-187.
Scalici et al.; "Circulating microRNAs in follicular fluid, powerful tools to explore in vitro fertilization process" Scientific Reports, vol. 6, No. 1, Apr. 22, 2016, entire document.
Shi; "Endometrial MicroRNA Signature during the Window of Implantation Changed in Patients with Repeated Implantation Failure"; Chinese Medical Journal March, Mar. 5, 2017, p. 566.
Yu et al.; "MicroRNAome in decidua: a new approach to assess the maintenance of pregnancy"; Fertility and Sterility; vol. 103, No. 4, Apr. 2015, p. 980.

* cited by examiner

*Primary Examiner* — Amanda Haney
(74) *Attorney, Agent, or Firm* — W & C IP

(57) ABSTRACT

The invention relates to a method of assessing pregnancy outcome. The inventors investigated endometrial miRNAs associated with pregnancy outcome by studying miRNAs associated with endometrial receptivity, implantation failure and embryo miscarriage. They performed a miRNomic study to find miRNAs that are differentially expressed according to the endometrial receptivity status, compared the endometrial miRNome between receptive patients with negative beta-hCG and receptive patients with positive beta-hCG, and compared the endometrial miRNome between receptive patients with a miscarriage between 8-12 weeks of amenorrhoea and receptive patients with a live birth. They demonstrated miRNA differential expression in endometrial samples according to the pregnancy outcome. Thus, the invention relates to a method of assessing pregnancy outcome of a patient, comprising a step of measuring in a biological sample obtained from the patient the expression level of at least one miRNA selected from the group consisting of miR-455-3 p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3 p, miR-320c, let-7d-5p, miR-125a-5p, miR-320a, miR-320b and let-7f-5p.

4 Claims, 4 Drawing Sheets

METHODS FOR ASSESSING PREGNANCY OUTCOME

FIELD OF THE INVENTION

Figure 1:
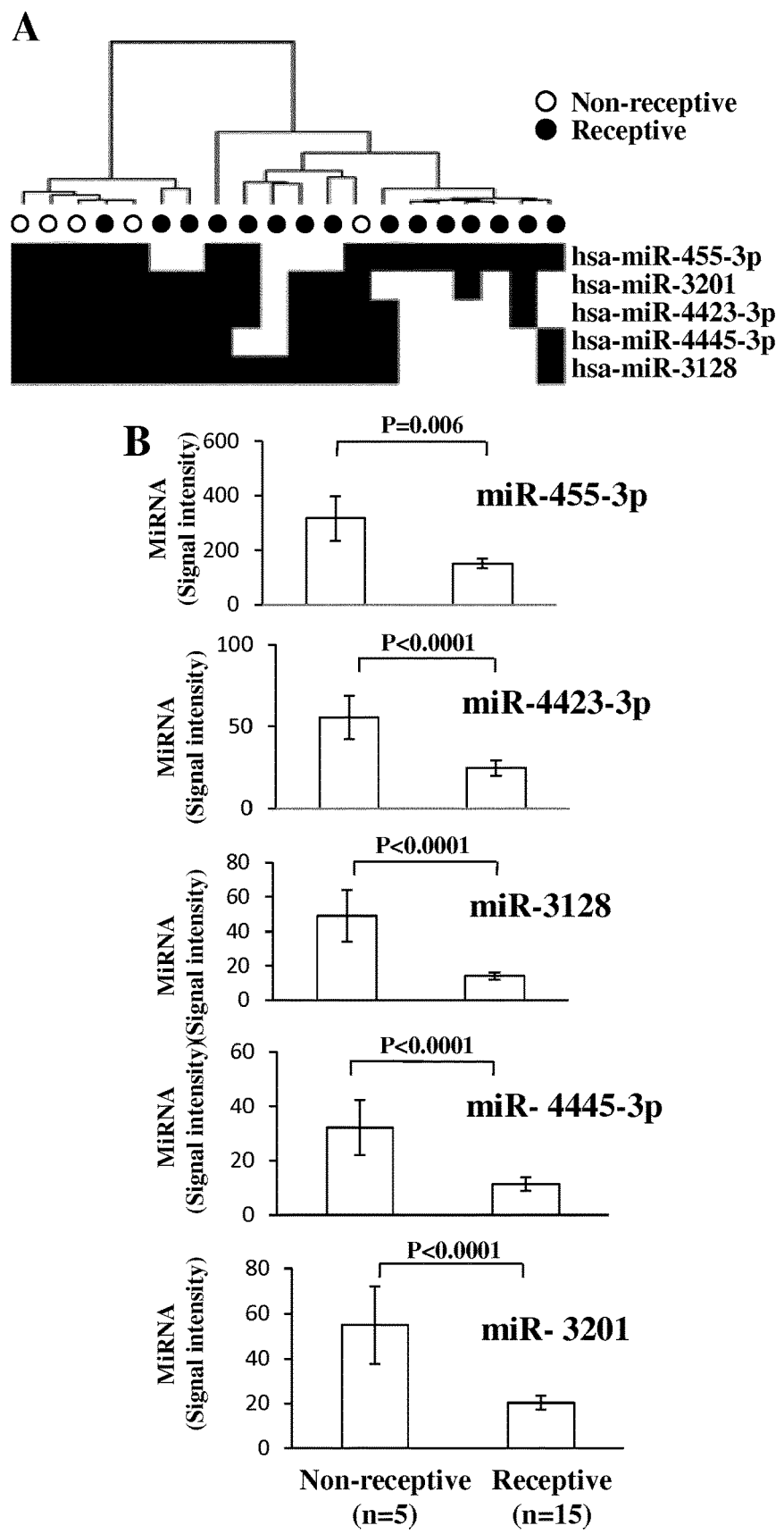

The present invention relates generally to the fields of reproductive medicine. More specifically, the present invention relates to methods for assessing pregnancy outcome of a patient.

BACKGROUND OF THE INVENTION

The assessment of endometrial receptivity is a crucial step before embryo transfer during assisted reproductive technology (ART) procedures. Indeed, the determination of the appropriate timing for embryo transfer, in the respect of the synchronization of the dialogue between embryo and endometrium, improves the pregnancy rate. Using our transcriptomic data (1-5), we previously identified specific genes that are overexpressed in the endometrium during the implantation window in human and that can be considered as potential biomarkers of human endometrial receptivity. After RT-qPCR validation of these transcriptomic results, we tested these endometrial receptivity biomarkers in fertile patients and in an ex vivo model (i.e., stromal and epithelial endometrium cells) (1-5). Consequently, we developed a test based on the quantification of these biomarkers in endometrium biopsies by RT-qPCR that we called Window Implantation Test (Win-Test) (Patent EP10305561.2; PCT/EP2011/058757). The 'Win-Test' allows determining with extreme precision the adequate embryo transfer time during natural or hormone-supplemented (HST) cycles by classifying endometrial samples as 'receptive', 'partially receptive' or 'non-receptive'. Embryo transfer is then performed at the blastocyst stage if the endometrium is 'receptive', or at day 2 or day 3 post-fertilization when the endometrium is partially receptivity. For non-receptive samples, a second evaluation is proposed later during the ART process, based on the results of the first Win-Test.

The Win-Test has improved ART outcomes in our hospital. Nevertheless, it is an invasive test that requires the collection of endometrium samples. Today, one of the top priorities of reproductive medicine is the development of non-invasive tests for endometrial receptivity and for predicting ART outcomes. MicroRNAs (miRNAs) are small non-coding RNA transcripts that regulate cell function by modulating the post-transcriptional activity of multiple target genes through repression of mRNA translation or regulation of mRNA degradation. Several evidences indicate that many miRNAs are crucial for cellular processes that occur during the cyclic endometrium changes (6-11). Moreover, aberrant miRNA expression has been associated with human endometrial disorders, such as endometriosis and carcinoma (12-15). As some miRNAs can be quantified in serum and plasma, the identification of endometrial receptivity-associated miRNAs in endometrial biopsies and also in blood samples could open new avenues for the development of non-invasive tests. The clinical utility of miRNAs as diagnostic/prognostic biomarkers has been demonstrated in several diseases, including life-threatening pathologies, by numerous studies using surgical specimens and biopsies as well as whole blood samples or specific blood components (16, 17).

With the aim of identifying endometrial miRNAs associated with pregnancy outcome, the inventors investigated endometrial miRNAs associated with endometrial receptivity, implantation failure and early embryo miscarriage. The inventors performed a miRNomic study to find miRNAs that are differentially expressed according to the endometrial receptivity status and the in vitro fertilization (IVF) outcome after personalized embryo transfer with the Win-test. More precisely, the inventors investigated the endometrial miRNome of endometrium samples according to the receptivity status, compared the endometrial miRNome between receptive patients with negative beta-hCG and receptive patients with positive beta-hCG, and compared the endometrial miRNome between receptive patients with a miscarriage between 8-12 weeks of amenorrhoea (n=5) and receptive patients with a live birth (n=5) after personalized embryo replacement.

SUMMARY OF THE INVENTION

The present invention relates generally to the fields of reproductive medicine. More specifically, the present invention relates to a method of assessing pregnancy outcome of a patient, comprising measuring in a biological sample obtained from said patient the expression level of at least one miRNA selected from the group consisting of miR-455-3p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3p, miR-320c, let-7d-5p, miR-125a-5p, miR-320a, miR-320b and let-7f-5p. In particular, the present invention is defined by the claims.

DETAILED DESCRIPTION OF THE INVENTION

The inventors investigated endometrial miRNAs associated with pregnancy outcome by studying endometrial miRNAs associated with endometrial receptivity, implantation failure and early embryo miscarriage. The inventors performed a miRNomic study to find miRNAs that are differentially expressed according to the endometrial receptivity status and the in vitro fertilization (IVF) outcome after personalized embryo transfer. The inventors also investigated the endometrial miRNome of endometrium samples according to the receptivity status, compared the endometrial miRNome between receptive patients with negative beta-hCG and receptive patients with positive beta-hCG, and compared the endometrial miRNome between receptive patients with a miscarriage between 8-12 weeks of amenorrhoea (n=5) and receptive patients with a live birth (n=5) after personalized embryo replacement.

The inventors demonstrated miRNA differential expression in endometrial samples according to the pregnancy outcome.

Accordingly, the present invention relates to a method of assessing pregnancy outcome of a patient, comprising a step of measuring in a biological sample obtained from said patient the expression level of at least one miRNA selected from the group consisting of miR-455-3p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3p, miR-320c, let-7d-5p, miR-125a-5p, miR-320a, miR-320b and let-7f-5p.

In some embodiments, the expression level of 1, 2, 3, 4, 5, 6, 7, 8, 9, 10, 11, 12, 13, 14, 15, 16, 17, 18, 19 or 20 miRNA selected from the group consisting of miR-455-3p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3p, miR-320c, let-7d-5p, miR-125a-5p, miR-320a, miR-320b and let-7f-5p is measured.

In some embodiments, the expression level of the 20 miRNA of the group consisting of miR-455-3p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3p, miR-320c, let-7d-5p, miR-125a-5p, miR-320a, miR-320b and let-7f-5p is measured.

As used herein the term "patient" refers to a mammalian female to which the present invention may be applied. Typically said mammal is a human (i.e a woman), but may concern other mammals such as primates, dogs, cats, pigs, sheep, cows.

As used herein the term "pregnancy outcome" has its general meaning in the art and refers to the final result of a fertilization event and the likelihood of the pregnancy being taken to term a viable birth. The term "pregnancy outcome" also refers to successful pregnancy. The term "pregnancy outcome" also refers to high implantation rate of embryo leading to pregnancy. The term "high implantation rate" means the potential of the embryo when transferred in uterus, to be implanted in the uterine environment and to give rise to a viable foetus, which in turn develops into a viable offspring absent a procedure or event that terminates said pregnancy. The term "pregnancy outcome" also refers to successful endometrial receptivity, absent of implantation failure and early embryo miscarriage. The term "endometrial receptivity" is a period in which the endometrium acquires a functional status that allows blastocyst adhesion and that will lead to successful pregnancy.

The term "biological sample" refers to blood, serum, plasma, endometrial cell or endometrial biopsy sample obtained from the patient. Said sample is obtained for the purpose of the in vitro evaluation. In some embodiment, the term "biological sample" refers to blood, serum, plasma, endometrial cell or endometrial biopsy sample obtained from the patient obtained during the implantation window between Pg+5 to Pg+8 (Pg, Progesterone) under hormone-supplemented (HST) cycles and between LH+6 to LH+9 under natural cycle such as described in the example.

As used herein, the term "miR" has its general meaning in the art and refers to the miRNA sequence publicly available from the data base http://microrna.sanger.ac.uk/sequences/ under the miRBase Accession number. The miRNAs of the invention are listed in Table 1:

TABLE 1 list of the miRNAs according to the invention

| miRNA | miRBase Accession number |
|---|---|
| miR-455-3p | MIMAT0004784 |
| miR-4423-3p | MIMAT0018936 |
| miR-4445-3p | MIMAT0018964 |
| miR-3128 | MIMAT0014991 |
| miR-3201 | MIMAT0015086 |
| let-7b-5p | MIMAT0000063 |
| let-7c-5p | MIMAT0000064 |
| miR-4534 | MIMAT0019073 |
| miR-214-3p | MIMAT0000271 |
| miR-15b-5p | MIMAT0000417 |
| miR-424-3p | MIMAT0004749 |
| miR-181a-5p | MIMAT0000256 |
| miR-574-3p | MIMAT0003239 |
| miR-92a-3p | MIMAT0000092 |
| miR-320c | MIMAT0005793 |
| let-7d-5p | MIMAT0000065 |
| miR-125a-5p | MIMAT0000443 |
| miR-320a | MIMAT0000510 |

TABLE 1-continued list of the miRNAs according to the invention

| miRNA | miRBase Accession number |
|---|---|
| miR-320b | MIMAT0005792 |
| let-7f-5p | MIMAT0000067 |

In a further aspect, the present invention relates to a method of assessing endometrial receptivity of a patient, comprising a step of measuring in a biological sample obtained from said patient the expression level of at least one miRNA selected from the group consisting of miR-455-3p, miR-4423-3p, miR-4445-3p, miR-3128 and miR-3201.

In some embodiments, the expression level of 1, 2, 3, 4 or 5 miRNA selected from the group consisting of miR-455-3p, miR-4423-3p, miR-4445-3p, miR-3128 and miR-3201 is determined. In some embodiments, the expression levels of miR-455-3p, miR-4423-3p, miR-4445-3p, miR-3128 and miR-3201 are measured.

In a further aspect, the present invention relates to a method of assessing implantation failure of a patient, comprising a step of measuring in a biological sample obtained from said patient the expression level of at least one miRNA selected from the group consisting of let-7b-5p, let-7c-5p, miR-4534, miR-214-3p, miR-15b-5p and miR-424-3p.

In some embodiments, the expression level of 1, 2, 3, 4, 5 or 6 miRNA selected from the group consisting of let-7b-5p, let-7c-5p, miR-4534, miR-214-3p, miR-15b-5p and miR-424-3p is determined. In some embodiments, the expression levels of let-7b-5p, let-7c-5p, miR-4534, miR-214-3p, miR-15b-5p and miR-424-3p are measured.

In a further aspect, the present invention relates to a method of assessing embryo miscarriage in a patient, comprising a step of measuring in a biological sample obtained from said patient the expression level of at least one miRNA selected from the group consisting of miR-181a-5p, miR-574-3p, miR-92a-3p, miR-320c, let-7d-5p, miR-125a-5p, miR-320a, miR-320b and let-7f-5p.

In some embodiments, the expression level of 1, 2, 3, 4, 5, 6, 7, 8 or 9 miRNA selected from the group consisting of miR-181a-5p, miR-574-3p, miR-92a-3p, miR-320c, let-7d-5p, miR-125a-5p, miR-320a, miR-320b and let-7f-5p is determined. In some embodiments, the expression levels of miR-181a-5p, miR-574-3p, miR-92a-3p, miR-320c, let-7d-5p, miR-125a-5p, miR-320a, miR-320b and let-7f-5p are measured.

The method of the invention may further comprise a step consisting of comparing the expression level of at least one miRNA in the biological sample with a reference value, wherein detecting differential in the expression level of the miRNA between the biological sample and the reference value is indicative of pregnancy outcome.

A reference value is determined for each miRNA. Typically, the reference value can be a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skill in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the miRNAs expression levels (obtained according to the method of the invention with a defined threshold value). In one embodiment of the present invention, the threshold value is derived from the miRNA expression level (or ratio, or score) determined in a biological sample derived from one or more patients with a high potential for pregnancy outcome. In one embodiment of the present invention, the threshold value may also be derived from the miRNA expression level (or ratio, or score) determined in a biological sample derived from one or more patients with a low potential for pregnancy outcome. Furthermore, retrospective measurement of the miRNA expression levels (or ratio, or scores) in properly banked historical patient samples may be used in establishing these threshold values.

In some embodiments, the reference value may be determined by carrying out a method comprising the steps of a) providing a collection of biological samples obtained from patients during the implantation window, b) providing, for each sample provided at step a), information relating to the actual clinical outcome (pregnancy or no pregnancy); c) providing a series of arbitrary quantification values; d) determining the level of the miRNA for each sample contained in the collection provided at step a); e) classifying said samples in two groups for one specific arbitrary quantification value provided at step c), respectively: (i) a first group comprising samples that exhibit a quantification value for the level that is lower than the said arbitrary quantification value contained in the said series of quantification values; (ii) a second group comprising samples that exhibit a quantification value for said level that is higher than the said arbitrary quantification value contained in the said series of quantification values; whereby two groups of samples are obtained for the said specific quantification value, wherein the samples of each group are separately enumerated; f) calculating the statistical significance between (i) the quantification value obtained at step e) and (ii) the actual clinical outcome of the patients (i.e. pregnancy or no pregnancy) from which samples contained in the first and second groups defined at step f) derive; g) reiterating steps f) and g) until every arbitrary quantification value provided at step d) is tested; and h) setting the said reference value as consisting of the arbitrary quantification value for which the highest statistical significance (most significant) has been calculated at step g).

For example, the level of the miRNA has been assessed for 100 samples of 100 patients. The 100 samples are ranked according to the level of the miRNA. Sample 1 has the highest level and sample 100 has the lowest level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding patients, the p value between both subsets was calculated. The reference value is then selected such as the discrimination based on the criterion of the minimum p value is the strongest. In other terms, the level of the miRNA corresponding to the boundary between both subsets for which the p value is minimum is considered as the reference value. It should be noted that the reference value is not necessarily the median value of levels of the miRNA.

The setting of a single "cut-off" value thus allows discrimination between with a high potential for pregnancy outcome or low potential for pregnancy outcome. Practically, high statistical significance values (e.g. low P values) are generally obtained for a range of successive arbitrary quantification values, and not only for a single arbitrary quantification value. Thus, in one alternative embodiment of the invention, instead of using a definite reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. For example, on a hypothetical scale of 1 to 10, if the ideal cut-off value (the value with the highest statistical significance) is 5, a suitable (exemplary) range may be from 4-6. Therefore, a patient may be assessed by comparing values obtained by measuring the level of the miRNA, where values greater than 5 reveal that the patient will be with a low potential for pregnancy outcome (or alternatively a with a high potential for pregnancy outcome) and values less than 5 reveal that the patient will be a with a high potential for pregnancy outcome (or alternatively with a low potential for pregnancy outcome). In another embodiment, a patient may be assessed by comparing values obtained by measuring the level of the miRNA and comparing the values on a scale, where values above the range of 4-6 indicate that the patient will be a with a low potential for pregnancy outcome (or alternatively a with a high potential for pregnancy outcome) and values below the range of 4-6 indicate that the patient will be a with a high potential for pregnancy outcome (or alternatively a with a low potential for pregnancy outcome), with values falling within the range of 4-6 indicating an intermediate pregnancy outcome.

In some embodiments, a score which is a composite of the expression levels of the different miRNAs may also be determined and compared to a reference value wherein a difference between said score and said reference value is indicative whether said patient with a high potential for pregnancy outcome or with a low potential for pregnancy outcome.

In some embodiments, the method of the invention comprises the step of determining the patient pregnancy outcome using a classification algorithm selected from Linear Discriminant Analysis (LDA), Topological Data Analysis (TDA), Neural Networks and Random Forests algorithm (RF). As used herein, the term "classification algorithm" has its general meaning in the art and refers to classification and regression tree methods and multivariate classification well known in the art such as described in U.S. Pat. No. 8,126,690; WO2008/156617. As used herein, the term "Random Forests algorithm" or "RF" has its general meaning in the art and refers to classification algorithm such as described in U.S. Pat. No. 8,126,690; WO2008/156617. Random Forest is a decision-tree-based classifier that is constructed using an algorithm originally developed by Leo Breiman (Breiman L, "Random forests," Machine Learning 2001, 45:5-32). The classifier uses a large number of individual decision trees and decides the class by choosing the mode of the classes as determined by the individual trees. The individual trees are constructed using the following algorithm: (1) Assume that the number of cases in the training set is N, and that the number of variables in the classifier is M; (2) Select the number of input variables that will be used to determine the decision at a node of the tree; this number, m should be much less than M; (3) Choose a training set by choosing N samples from the training set with replacement; (4) For each node of the tree randomly select m of the M variables on which to base the decision at that node; (5) Calculate the best split based on these m variables in the training set. In some embodiments, the score is generated by a computer program.

In some embodiments, a higher expression level of at least one miRNA selected from the group consisting of miR-455-3p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3p, miR-320c, let-7d-5p, miR-125a-5p, miR-320a, miR-320b and let-7f-5p are indicative of low potential for pregnancy outcome, and accordingly a lower expression level of at least one miRNA selected from the group consisting of miR-455-3p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3p, miR-320c, let-7d-5p, miR-125a-5p, miR-320a, miR-320b and let-7f-5p are indicative of high potential for pregnancy outcome.

In some embodiments, the reference value may correspond to the expression level determined in a biological sample associated with a high potential for pregnancy outcome. Accordingly, a higher expression level of at least one miRNA selected from the group consisting of miR-455-3p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3p, miR-320c, let-7d-5p, miR-125a-5p, miR-320a, miR-320b and let-7f-5p than the reference value is indicative of low potential for pregnancy outcome, and a lower or equal expression level of at least one miRNA selected from the group consisting of miR-455-3p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3p, miR-320c, let-7d-5p, miR-125a-5p, miR-320a, miR-320b and let-7f-5p than the reference value is indicative of high potential for pregnancy outcome.

In some embodiments, the reference value may correspond to the expression level determined in a biological sample associated with a low potential for pregnancy outcome. Accordingly, a higher or equal expression level of at least one miRNA selected from the group consisting of miR-455-3p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3p, miR-320c, let-7d-5p, miR-125a-5p, miR-320a, miR-320b and let-7f-5p than the reference value is indicative of low potential for pregnancy outcome, and a lower expression level of at least one miRNA selected from the group consisting of miR-455-3p, miR-4423-3p, miR-4445-3p, miR-3128, miR-3201, let-7b-5p, let-7c-5p, miR-4534, miR-214-3p, miR-15b-5p, miR-424-3p, miR-181a-5p, miR-574-3p, miR-92a-3p, miR-320c, let-7d-5p, miR-125a-5p, miR-320a, miR-320b and let-7f-5p than the reference value is indicative of high potential for pregnancy outcome.

In some embodiments, the reference value may correspond to the expression level determined in a biological sample associated with a receptive endometrium. Accordingly, a higher expression level of at least one miRNA selected from the group consisting of miR-455-3p, miR-4423-3p, miR-4445-3p, miR-3128 and miR-3201 than the reference value is indicative of non-receptive endometrium, and a lower or equal expression level of at least one miRNA selected from the group consisting of miR-455-3p, miR-4423-3p, miR-4445-3p, miR-3128 and miR-3201 than the reference value is indicative of receptive endometrium.

In some embodiments, the reference value may correspond to the expression level determined in a biological sample associated with a non-receptive endometrium. Accordingly, a higher or equal expression level of at least one miRNA selected from the group consisting of miR-455-3p, miR-4423-3p, miR-4445-3p, miR-3128 and miR-3201 than the reference value is indicative of non-receptive endometrium, and a lower expression level of at least one miRNA selected from the group consisting of miR-455-3p, miR-4423-3p, miR-4445-3p, miR-3128 and miR-3201 than the reference value is indicative of receptive endometrium.

In some embodiments, the reference value may correspond to the expression level determined in a biological sample associated with absence of implantation failure. Accordingly, a higher expression level of at least one miRNA selected from the group consisting of let-7b-5p, let-7c-5p, miR-4534, miR-214-3p, miR-15b-5p and miR-424-3p than the reference value is indicative of implantation failure, and a lower or equal expression level of at least one miRNA selected from the group consisting of let-7b-5p, let-7c-5p, miR-4534, miR-214-3p, miR-15b-5p and miR-424-3p than the reference value is indicative of absence of implantation failure.

In some embodiments, the reference value may correspond to the expression level determined in a biological sample associated with implantation failure. Accordingly, a higher or equal expression level of at least one miRNA selected from the group consisting of let-7b-5p, let-7c-5p, miR-4534, miR-214-3p, miR-15b-5p and miR-424-3pthan the reference value is indicative of implantation failure, and a lower expression level of at least one miRNA selected from the group consisting of let-7b-5p, let-7c-5p, miR-4534, miR-214-3p, miR-15b-5p and miR-424-3p than the reference value is indicative of absence of implantation failure.

In some embodiments, the reference value may correspond to the expression level determined in a biological sample associated with absence of embryo miscarriage. Accordingly, a higher expression level of at least one miRNA selected from the group consisting of miR-181a-5p, miR-574-3p, miR-92a-3p, miR-320c, let-7d-5p, miR-125a-5p, miR-320a, miR-320b and let-7f-5p than the reference value is indicative of embryo miscarriage, and a lower or equal expression level of at least one miRNA selected from the group consisting of miR-181a-5p, miR-574-3p, miR-92a-3p, miR-320c, let-7d-5p, miR-125a-5p, miR-320a, miR-320b and let-7f-5p than the reference value is indicative of absence of embryo miscarriage.

In some embodiments, the reference value may correspond to the expression level determined in a biological sample associated with embryo miscarriage. Accordingly, a higher or equal expression level of at least one miRNA selected from the group consisting of miR-181a-5p, miR-574-3p, miR-92a-3p, miR-320c, let-7d-5p, miR-125a-5p, miR-320a, miR-320b and let-7f-5p than the reference value is indicative of embryo miscarriage, and a lower expression level of at least one miRNA selected from the group consisting of miR-181a-5p, miR-574-3p, miR-92a-3p, miR-320c, let-7d-5p, miR-125a-5p, miR-320a, miR-320b and let-7f-5p than the reference value is indicative of absence of embryo miscarriage.

According to the invention, measuring the expression level of the miRNA selected from the group consisting of miRNAs of Table A of the invention in the biological sample obtained from the patient can be performed by a variety of techniques. For example the nucleic acid contained in the samples (biological sample prepared from the patient) is first extracted according to standard methods, for example using lytic enzymes or chemical solutions or extracted by nucleic-acid-binding resins following the manufacturer's instructions. Conventional methods and reagents for isolating RNA from a biological sample comprise High Pure miRNA Isolation Kit (Roche), Trizol (Invitrogen), Guanidinium thiocyanate-phenol-chloroform extraction, PureLink™ miRNA isolation kit (Invitrogen), PureLink Micro-to-Midi Total RNA Purification System (invitrogen), RNeasy kit (Qiagen), miRNeasy kit (Qiagen), Oligotex kit (Qiagen), phenol extraction, phenol-chloroform extraction, TCA/acetone precipitation, ethanol precipitation, Column purification, Silica gel membrane purification, PureYield™ RNA Midiprep (Promega), PolyATtract System 1000 (Promega), Maxwell® 16 System (Promega), SV Total RNA Isolation (Promega), geneMAG-RNA/DNA kit (Chemicell), TRI Reagent® (Ambion), RNAqueous Kit (Ambion), ToTALLY RNA™ Kit (Ambion), Poly(A)Purist™ Kit (Ambion) and any other methods, commercially available or not, known to the skilled person. The expression level of one or more miRNA in the biological sample may be determined by any suitable method. Any reliable method for measuring the level or amount of miRNA in a sample may be used. Generally, miRNA can be detected and quantified from a biological sample (including fractions thereof), such as samples of isolated RNA by various methods known for mRNA, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), NanoString analysis, Northern Blot analysis, branched DNA (bDNA) signal amplification, in situ hybridization, etc.), and sequencing-based methods (e.g., next-generation sequencing methods, for example, using the Illumina or IonTorrent platforms). Other exemplary techniques include ribonuclease protection assay (RPA) and mass spectroscopy.

In some embodiments, RNA is converted to DNA (cDNA) prior to analysis. cDNA can be generated by reverse transcription of isolated miRNA using conventional techniques. miRNA reverse transcription kits are known and commercially available. Examples of suitable kits include, but are not limited to the mirVanaTaqMan0 miRNA transcription kit (Ambion, Austin, Tex.), and the TaqMan® miRNA transcription kit (Applied Biosystems, Foster City, Calif.). Universal primers, or specific primers, including miRNA-specific stem-loop primers, are known and commercially available, for example, from Applied Biosystems. In some embodiments, miRNA is amplified prior to measurement. In some embodiments, the expression level of miRNA is measured during the amplification process. In some embodiments, the expression level of miRNA is not amplified prior to measurement. Some exemplary methods suitable for determining the expression level of miRNA in a sample are described in greater hereinafter. These methods are provided by way of illustration only, and it will be apparent to a skilled person that other suitable methods may likewise be used.

Many amplification-based methods exist for detecting the expression level of miRNA nucleic acid sequences, including, but not limited to, PCR, RT-PCR, qPCR, and rolling circle amplification. Other amplification-based techniques include, for example, ligase chain reaction (LCR), multiplex ligatable probe amplification, in vitro transcription (IVT), strand displacement amplification (SDA), transcription-mediated amplification (TMA), nucleic acid sequence based amplification (NASBA), RNA (Eberwine) amplification, and other methods that are known to persons skilled in the art. A typical PCR reaction includes multiple steps, or cycles, that selectively amplify target nucleic acid species: a denaturing step, in which a target nucleic acid is denatured; an annealing step, in which a set of PCR primers (i.e., forward and reverse primers) anneal to complementary DNA strands, and an elongation step, in which a thermostable DNA polymerase elongates the primers. By repeating these steps multiple times, a DNA fragment is amplified to produce an amplicon, corresponding to the target sequence. Typical PCR reactions include 20 or more cycles of denaturation, annealing, and elongation. In many cases, the annealing and elongation steps can be performed concurrently, in which case the cycle contains only two steps. A reverse transcription reaction (which produces a cDNA sequence having complementarity to a miRNA) may be performed prior to PCR amplification. Reverse transcription reactions include the use of, e.g., a RNA-based DNA polymerase (reverse transcriptase) and a primer. Kits for quantitative real time PCR of miRNA are known, and are commercially available. Examples of suitable kits include, but are not limited to, the TaqMan® miRNA Assay (Applied Biosystems) and the mirVana™ qRT-PCR miRNA detection kit (Ambion). The miRNA can be ligated to a single stranded oligonucleotide containing universal primer sequences, a polyadenylated sequence, or adaptor sequence prior to reverse transcriptase and amplified using a primer complementary to the universal primer sequence, poly(T) primer, or primer comprising a sequence that is complementary to the adaptor sequence. In some embodiments, custom qRT-PCR assays can be developed for determination of miRNA levels. Custom qRT-PCR assays to measure miRNAs in a sample can be developed using, for example, methods that involve an extended reverse transcription primer and locked nucleic acid modified PCR. Custom miRNA assays can be tested by running the assay on a dilution series of chemically synthesized miRNA corresponding to the target sequence. This permits determination of the limit of detection and linear range of quantitation of each assay. Furthermore, when used as a standard curve, these data permit an estimate of the absolute abundance of miRNAs measured in the samples. Amplification curves may optionally be checked to verify that Ct values are assessed in the linear range of each amplification plot. Typically, the linear range spans several orders of magnitude. For each candidate miRNA assayed, a chemically synthesized version of the miRNA can be obtained and analyzed in a dilution series to determine the limit of sensitivity of the assay, and the linear range of quantitation. Relative expression levels may be determined, for example, according to the 2(-ΔΔ C(T)) Method, as described by Livak et al., Analysis of relative gene expression data using real-time quantitative PCR and the 2(-ΔΔ C(T)) Method. Methods (2001) December; 25(4):402-8.

In some embodiments, two or more miRNAs are amplified in a single reaction volume. For example, multiplex q-PCR, such as qRT-PCR, enables simultaneous amplification and quantification of at least two miRNAs of interest in one reaction volume by using more than one pair of primers and/or more than one probe. The primer pairs comprise at least one amplification primer that specifically binds each miRNA, and the probes are labeled such that they are distinguishable from one another, thus allowing simultaneous quantification of multiple miRNAs.

Rolling circle amplification is a DNA-polymerase driven reaction that can replicate circularized oligonucleotide probes with either linear or geometric kinetics under isothermal conditions (see, for example, Lizardi et al., Nat. Gen. (1998) 19(3):225-232; Gusev et al., Am. J. Pathol. (2001) 159(0:63-69; Nallur et al., Nucleic Acids Res. (2001) 29(23):E118). In the presence of two primers, one hybridizing to the (+) strand of DNA, and the other hybridizing to the (−) strand, a complex pattern of strand displacement results in the generation of over 109 copies of each DNA molecule in 90 minutes or less. Tandemly linked copies of a closed circle DNA molecule may be formed by using a single primer. The process can also be performed using a matrix-associated DNA. The template used for rolling circle amplification may be reverse transcribed. This method can be used as a highly sensitive indicator of miRNA sequence and expression level at very low miRNA concentrations (see, for example, Cheng et al., Angew Chem. Int. Ed. Engl. (2009) 48(18):3268-72; Neubacher et al., Chembiochem. (2009) 10(8): 1289-91).

miRNA quantification may be performed by using stem-loop primers for reverse transcription (RT) followed by a real-time TaqMan® probe. Typically, said method comprises a first step wherein the stem-loop primers are annealed to miRNA targets and extended in the presence of reverse transcriptase. Then miRNA-specific forward primer, TaqMan® probe, and reverse primer are used for PCR reactions. Quantitation of miRNAs is estimated based on measured CT values. Many miRNA quantification assays are commercially available from Qiagen (S. A. Courtaboeuf, France), Exiqon (Vedbaek, Denmark) or Applied Biosystems (Foster City, USA).

Expression levels of miRNAs may be expressed as absolute expression levels or normalized expression levels. Typically, expression levels are normalized by correcting the absolute expression level of miRNAs by comparing its expression to the expression of a mRNA that is not a relevant marker for determining pregnancy outcome of a patient, e.g., a housekeeping mRNA that is constitutively expressed. Suitable mRNAs for normalization include housekeeping mRNAs such as the U6, U24, U48 and S18. This normalization allows the comparison of the expression level in one sample, e.g., a patient sample, to another sample, or between samples from different sources. In a particular embodiment, expression levels are normalized by correcting the absolute expression level of miRNAs by comparing its expression to the expression of a reference mRNA.

Nucleic acids exhibiting sequence complementarity or homology to the miRNAs of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

The probes and primers are "specific" to the miRNAs they hybridize to, i.e. they preferably hybridize under high stringency hybridization conditions (corresponding to the highest melting temperature Tm, e.g., 50% formamide, 5× or 6× SCC. SCC is a 0.15 M NaCl, 0.015 M Na-citrate).

miRNA may be detected using hybridization-based methods, including but not limited to hybridization arrays (e.g., microarrays), NanoString analysis, Northern Blot analysis, branched DNA (bDNA) signal amplification, and in situ hybridization.

Microarrays can be used to measure the expression levels of large numbers of miRNAs simultaneously. Microarrays can be fabricated using a variety of technologies, including printing with fine-pointed pins onto glass slides, photolithography using pre-made masks, photolithography using dynamic micromirror devices, inkjet printing, or electrochemistry on microelectrode arrays. Also useful are microfluidic TaqMan Low-Density Arrays, which are based on an array of microfluidic qRT-PCR reactions, as well as related microfluidic qRT-PCR based methods. In one example of microarray detection, various oligonucleotides (e.g., 200+ 5'-amino-modified-C6 oligos) corresponding to human sense miRNA sequences are spotted on three dimensional CodeLink slides (GE Health/Amersham Biosciences) at a final concentration of about 20 µM and processed according to manufacturer's recommendations. First strand cDNA synthesized from 20 µg TRIzol-purified total RNA is labeled with biotinylated ddUTP using the Enzo BioArray end labeling kit (Enzo Life Sciences Inc.). Hybridization, staining, and washing can be performed according to a modified Affymetrix Antisense genome array protocol. Axon B-4000 scanner and Gene-Pix Pro 4.0 software or other suitable software can be used to scan images. Non-positive spots after background subtraction, and outliers detected by the ESD procedure, are removed. The resulting signal intensity values are normalized to per-chip median values and then used to obtain geometric means and standard errors for each miRNA. Each miRNA signal can be transformed to log base 2, and a one-sample t test can be conducted. Independent hybridizations for each sample can be performed on chips with each miRNA spotted multiple times to increase the robustness of the data.

Microarrays can be used for the expression profiling of miRNAs. For example, RNA can be extracted from the sample and, optionally, the miRNAs are size selected from total RNA. Oligonucleotide linkers can be attached to the 5' and 3' ends of the miRNAs and the resulting ligation products are used as templates for an RT-PCR reaction. The sense strand PCR primer can have a fluorophore attached to its 5' end, thereby labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA. Total RNA containing the miRNA extracted from the sample can also be used directly without size-selection of the miRNAs. For example, the RNA can be 3' end labeled using T4 RNA ligase and a fluorophore-labeled short RNA linker. Fluorophore-labeled miRNAs complementary to the corresponding miRNA capture probe sequences on the array hybridize, via base pairing, to the spot at which the capture probes are affixed. The fluorescence intensity of each spot is then evaluated in terms of the number of copies of a particular miRNA, using a number of positive and negative controls and array data normalization methods, which will result in assessment of the level of expression of a particular miRNA. Several types of microarrays can be employed including, but not limited to, spotted oligonucleotide microarrays, prefabricated oligonucleotide microarrays or spotted long oligonucleotide arrays.

Accordingly, the nucleic acid probes include one or more labels, for example to permit detection of a target nucleic acid molecule using the disclosed probes. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or concentration of a target nucleic acid sequence (e.g., genomic target nucleic acid sequence) (to which the labeled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultraviolet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook-A Guide to Fluorescent Probes and Labeling Technologies). Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2' disulfonic acid, acridine and derivatives such as acridine and acridineisothiocyanate, 5-(2'-aminoethyl) aminonaphthalene-1-sulfonic acid (EDANS), 4-amino-N-[3 vinylsulfonyl)phenyl]naphthalimide-3,5 disulfonate (Lucifer Yellow VS), N-(4-anilino-1-naphthyl)maleimide, Brilliant Yellow, coumarin and derivatives such as coumarin, 7-amino-4-methylcoumarin (AMC, Coumarin 120), 7-amino-4-trifluoromethylcoumarin (Coumarin 151); cyanosine; 4',6-diarninidino -2-phenylindole (DAPI); 5',5'' dibromopyrogallol-sulfonephthalein (Bromopyrogallol Red); 7-diethylamino -3-(4'-isothiocyanatophenyl)-4-methylcoumarin; diethylenetriaminepentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosinisothiocyanate; ethidium; fluorescein and derivatives such as 5-carboxyfluorescein (FAM), Dichlorotriazinylamino fluorescein (DTAF), 2'7'dimethoxy-4'5'-dichloro-6-carboxyfluorescein (JOE), fluorescein, fluorescein isothiocyanate (FITC), and QFITC Q(RITC); 2',7'-difluorofluorescein (OREGON GREEN®); fluorescamine; IR144; IR1446; Malachite Green isothiocyanate; 4-methylumbelliferone; orthocresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethylrhodamineisothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.) and including the ALEXA FLUOR® series of dyes (for example, as described in U.S. Pat. Nos. 5,696,157, 6,130,101 and 6,716, 979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (Quantum-Dot Corp, Invitrogen Nanocrystal Technologies, Eugene, Oreg.); see also, U.S. Pat. Nos. 6,815,064; 6,682,596; and 6,649, 138). Semiconductor nanocrystals are microscopic particles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. This emission can he detected as colored light of a specific wavelength or fluorescence. Semiconductor nanocrystals with different spectral characteristics are described in e.g., U.S. Pat. No. 6,602,671. Semiconductor nanocrystals that can he coupled to a variety of biological molecules (including dNTPs and/or nucleic acids) or substrates by techniques described in, for example, Bruchez et al., Science 281 :20132016, 1998; Chan et al., Science 281:2016-2018, 1998; and U.S. Pat. No. 6,274,323. Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can he produced that are identifiable based on their different spectral characteristics. For example, semiconductor nanocrystals can he produced that emit light of different colors based on their composition, size or size and composition. For example, quantum dots that emit light at different wavelengths based on size (565 nm, 655 nm, 705 nm, or 800 nm emission wavelengths), which are suitable as fluorescent labels in the probes disclosed herein are available from Life Technologies (Carlsbad, Calif.).

RT-PCR is typically carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and thermal polymerase. The majority of the thermocyclers on the market now offer similar characteristics. Typically, thermocyclers involve a format of glass capillaries, plastics tubes, 96-well plates or 384-well plates. The thermocylcer also involves software analysis.

miRNAs can also be detected without amplification using the nCounter Analysis System (NanoString Technologies, Seattle, Wash.). This technology employs two nucleic acid-based probes that hybridize in solution (e.g., a reporter probe and a capture probe). After hybridization, excess probes are removed, and probe/target complexes are analyzed in accordance with the manufacturer's protocol. nCounter miRNA assay kits are available from NanoString Technologies, which are capable of distinguishing between highly similar miRNAs with great specificity. The basis of the nCounter® Analysis system is the unique code assigned to each nucleic acid target to be assayed (International Patent Application Publication No. WO 08/124847, U.S. Pat. No. 8,415,102 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes is designed for each oligonucleotide target, a biotinylated capture probe and a reporter probe carrying the fluorescent barcode. This system is also referred to, herein, as the nanoreporter code system. Specific reporter and capture probes are synthesized for each target. The reporter probe can comprise at a least a first label attachment region to which are attached one or more label monomers that emit light constituting a first signal; at least a second label attachment region, which is non-over-lapping with the first label attachment region, to which are attached one or more label monomers that emit light constituting a second signal; and a first target-specific sequence. Preferably, each sequence specific reporter probe comprises a target specific sequence capable of hybridizing to no more than one gene and optionally comprises at least three, or at least four label attachment regions, said attachment regions comprising one or more label monomers that emit light, constituting at least a third signal, or at least a fourth signal, respectively. The capture probe can comprise a second target-specific sequence; and a first affinity tag. In some embodiments, the capture probe can also comprise one or more label attachment regions. Preferably, the first target-specific sequence of the reporter probe and the second target-specific sequence of the capture probe hybridize to different regions of the same gene to be detected. Reporter and capture probes are all pooled into a single hybridization mixture, the "probe library". The relative abundance of each target is measured in a single multiplexed hybridization reaction. The method comprises contacting the sample with a probe library, such that the presence of the target in the sample creates a probe pair-target complex. The complex is then purified. More specifically, the sample is combined with the probe library, and hybridization occurs in solution. After hybridization, the tripartite hybridized complexes (probe pairs and target) are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies). Purified reactions are typically deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The expression level of a target is measured by imaging each sample and counting the number of times the code for that target is detected. For each sample, typically 600 fields-of-view (FOV) are imaged (1376×1024 pixels) representing approximately 10 mm2 of the binding surface. Typical imaging density is 100-1200 counted reporters per field of view depending on the degree of multiplexing, the amount of sample input, and overall target abundance. Data is output in simple spreadsheet format listing the number of counts per target, per sample. This system can be used along with nanoreporters. Additional disclosure regarding nanoreporters can be found in International Publication No. WO 07/076129 and WO07/076132, and US Patent Publication No. 2010/0015607 and 2010/0261026, the contents of which are incorporated herein in their entireties. Further, the term nucleic acid probes and nanoreporters can include the rationally designed (e.g. synthetic sequences) described in International Publication No. WO 2010/019826 and US Patent Publication No. 2010/0047924, incorporated herein by reference in its entirety.

Mass spectroscopy can be used to quantify miRNA using RNase mapping. Isolated RNAs can be enzymatically digested with RNA endonucleases (RNases) having high specificity (e.g., RNase T1, which cleaves at the 3'-side of all unmodified guanosine residues) prior to their analysis by MS or tandem MS (MS/MS) approaches. The first approach developed utilized the on-line chromatographic separation of endonuclease digests by reversed phase HPLC coupled directly to ESTMS. The presence of post-transcriptional modifications can be revealed by mass shifts from those expected based upon the RNA sequence. Ions of anomalous mass/charge values can then be isolated for tandem MS sequencing to locate the sequence placement of the post-transcriptionally modified nucleoside. Matrix-assisted laser desorption/ionization mass spectrometry (MALDI-MS) has also been used as an analytical approach for obtaining information about post-transcriptionally modified nucleosides. MALDI-based approaches can be differentiated from EST-based approaches by the separation step. In MALDI-MS, the mass spectrometer is used to separate the miRNA. To analyze a limited quantity of intact miRNAs, a system of capillary LC coupled with nanoESI-MS can be employed, by using a linear ion trap-orbitrap hybrid mass spectrometer (LTQ Orbitrap XL, Thermo Fisher Scientific) or a tandem-quadrupole time-of-flight mass spectrometer (QSTAR® XL, Applied Biosystems) equipped with a custom-made nanospray ion source, a Nanovolume Valve (Valco Instruments), and a splitlessnano HPLC system (DiNa, KYA Technologies). Analyte/TEAA is loaded onto a nano-LC trap column, desalted, and then concentrated. Intact miRNAs are eluted from the trap column and directly injected into a CI 8 capillary column, and chromatographed by RP-HPLC using a gradient of solvents of increasing polarity. The chromatographic eluent is sprayed from a sprayer tip attached to the capillary column, using an ionization voltage that allows ions to be scanned in the negative polarity mode.

Additional methods for miRNA detection and measurement include, for example, strand invasion assay (Third Wave Technologies, Inc.), surface plasmon resonance (SPR), cDNA, MTDNA (metallic DNA; Advance Technologies, Saskatoon, SK), and single-molecule methods such as the one developed by US Genomics. Multiple miRNAs can be detected in a microarray format using a novel approach that combines a surface enzyme reaction with nanoparticle-amplified SPR imaging (SPRI). The surface reaction of poly(A) polymerase creates poly(A) tails on miRNAs hybridized onto locked nucleic acid (LNA) microarrays. DNA-modified nanoparticles are then adsorbed onto the poly(A) tails and detected with SPRI. This ultrasensitive nanoparticle-amplified SPRI methodology can be used for miRNA profiling at attamole levels. miRNAs can also be detected using branched DNA (bDNA) signal amplification (see, for example, Urdea, Nature Biotechnology (1994), 12:926-928). miRNA assays based on bDNA signal amplification are commercially available. One such assay is the QuantiGene® 2.0 miRNA Assay (Affymetrix, Santa Clara, Calif.). Northern Blot and in situ hybridization may also be used to detect miRNAs. Suitable methods for performing Northern Blot and in situ hybridization are known in the art. Advanced sequencing methods can likewise be used as available. For example, miRNAs can be detected using Illumina® Next Generation Sequencing (e.g. Sequencing-By-Synthesis or TruSeq methods, using, for example, the HiSeq, HiScan, GenomeAnalyzer, or MiSeq systems (Illumina, Inc., San Diego, Calif.). miRNAs can also be detected using Ion Torrent Sequencing (Ion Torrent Systems, Inc., Gulliford, Conn.), or other suitable methods of semiconductor sequencing.

A further object relates to a kit for performing the methods of the present invention, wherein said kit comprises means for measuring the expression level of at least one miRNA selected from miRNAs of Table A that is indicative of pregnancy outcome of a patient. Typically the kit may include primers, probes, macroarrays or microarrays as above described. For example, the kit may comprise a set of miRNA probes as above defined, usually made of DNA, and optionally pre-labelled. Alternatively, probes may be unlabelled and the ingredients for labelling may be included in the kit in separate containers. The kit may further comprise hybridization reagents or other suitably packaged reagents and materials needed for the particular hybridization protocol, including solid-phase matrices, if applicable, and standards. Alternatively the kit of the invention may comprise amplification primers (e.g. stem-loop primers) that may be pre-labelled or may contain an affinity purification or attachment moiety. The kit may further comprise amplification reagents and also other suitably packaged reagents and materials needed for the particular amplification protocol.

The method of the invention is particularly suitable for reaching a clinical decision. As used herein the term "clinical decision" refers to any decision to take or not take an action that has an outcome that affects the health or survival of the embryo. In particular, in the context of the invention, a clinical decision refers to a decision to implant or not the embryo of in the uterus of the patient. In particular the method as above described will thus help embryologist to avoid the transfer of embryos in uterus with a low potential for pregnancy outcome. The method as above described is also particularly suitable for enhancing pregnancy outcome. The method as above described is also particularly suitable for preventing or reducing the implantation failure or miscarriage. The method as above described is also particularly suitable for improving in vitro fertilization outcomes.

In a further aspect, the invention relates to a method for enhancing the pregnancy outcome of a patient comprising the steps consisting of i) assessing pregnancy outcome by performing the method according to the invention, and ii) implanting the embryo in the uterus of the patient if said patient has been determined as having high potential of pregnancy outcome.

The invention will be further illustrated by the following figures and examples. However, these examples and figures should not be interpreted in any way as limiting the scope of the present invention.

FIGURES

FIG. 1: Supervised classification with hierarchical clustering of 20 endometrium samples diagnosed as receptive or non-receptive during the theoretical implantation window (A). The microarray signals of each candidate (mean±SEM) are shown in (B).

Figure 2:
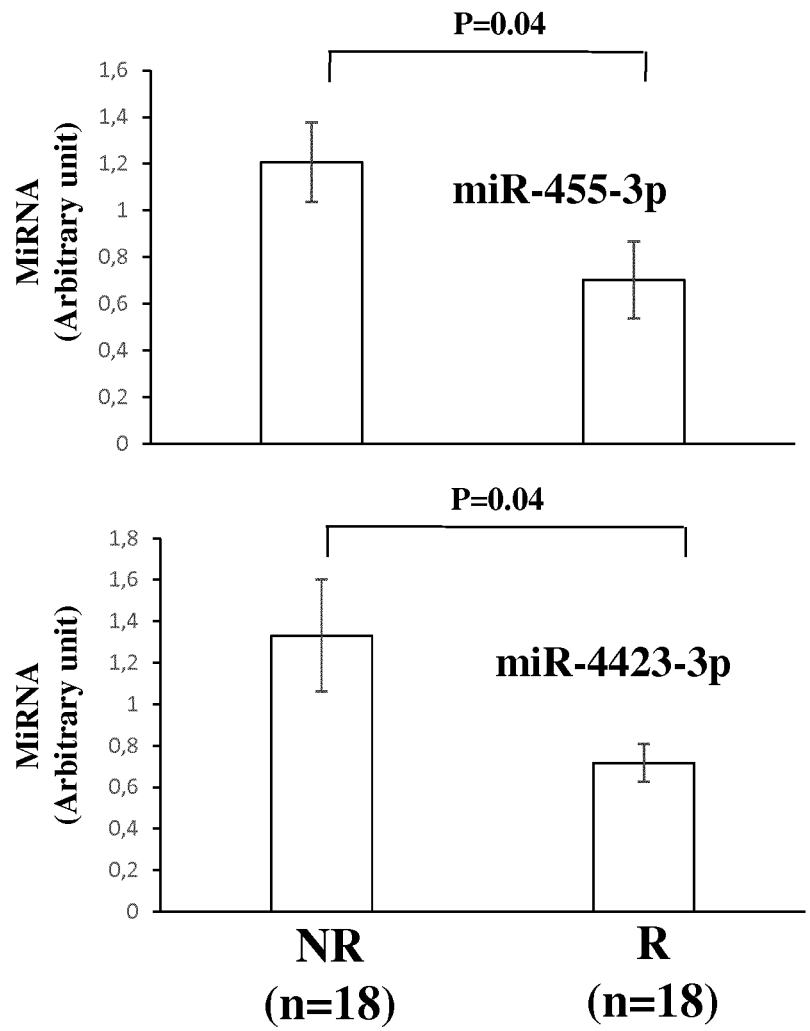

FIG. 2: RT-qPCR analyses of miR-4423-3p and miR-455-3p expression in endometrium samples from patients with RIF classified as receptive (R) or non-receptive (NR) using the Win-Test. MiR-4423-3p and miR-455-3p expression were calculated relative to miR-16-5p expression. The error bars represent the SEM.

Figure 3:
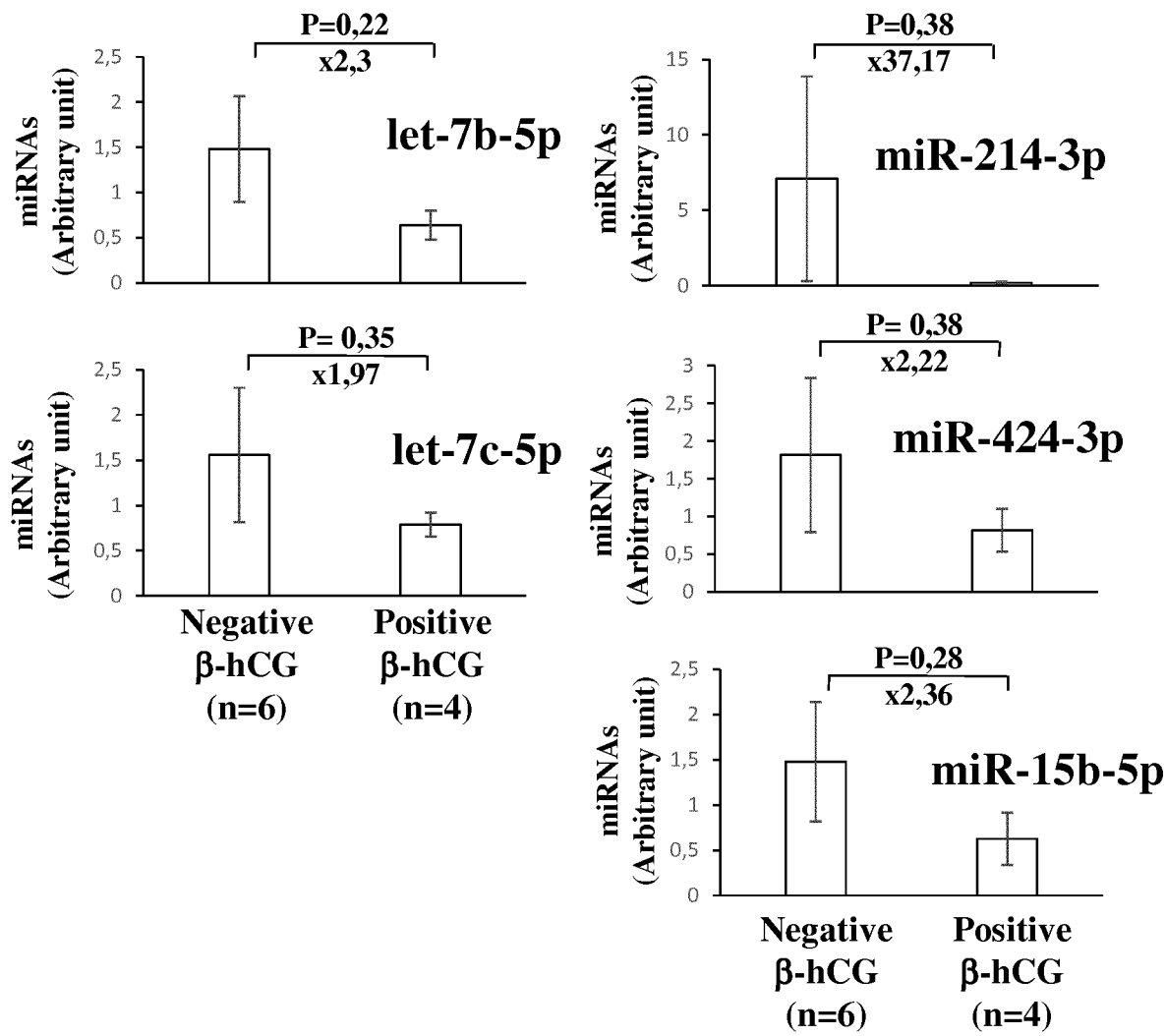

FIG. 3: RT-qPCR analyses of let-7c-5p, let-7b-5p, miR-214-3p, miR-15b-5p and miR-424-3p in serum samples from patients with a positive or negative β-hCG. miR-16-5p was used as housekeeping miRNA. The error bars represent the SEM.

Figure 4:
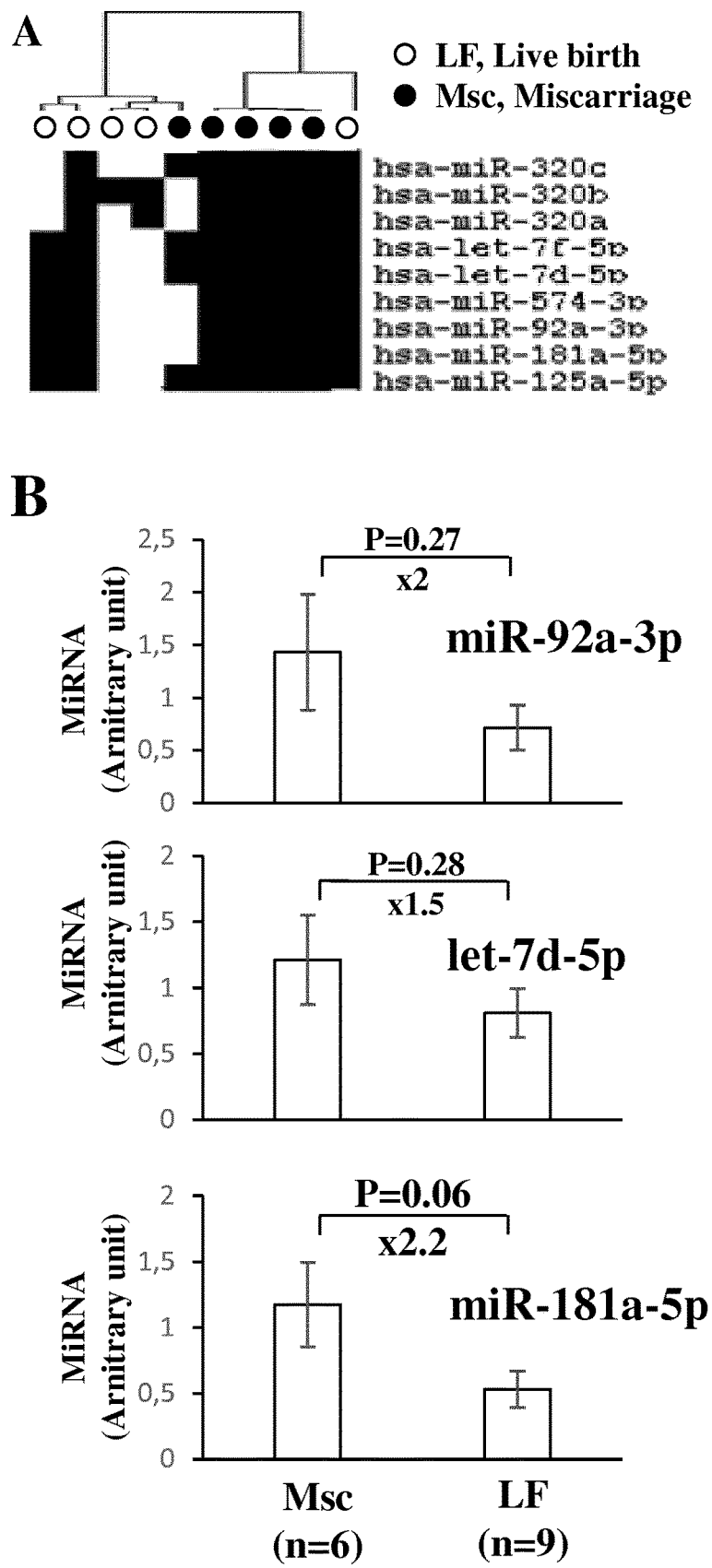

FIG. 4: Supervised classification with hierarchical clustering of 10 endometrium samples from patients with miscarriage and patients with life birth (A). RT-qPCR analyses of miR-181a-5p, miR-92a-3p and let-7d-5p in endometrial samples from patients with miscarriage and life birth. miR-16-5p was used as housekeeping miRNA (B). The error bars represent the SEM.

EXAMPLES

Example 1

Material & Methods
Study Design and Sample Collection

The study group comprised 40 infertile patients (mean±SEM, age: 37.1±0.9 years) with repeated implantation failures (RIFs).

All patients were recruited after written informed consent. These patients were under hormone replacement therapy (HRT) awaiting for replacement of cryopreserved after history of RIFs (≥3) after cryopreserved embryo replacement. HRT regimen involved either a daily oral dose of 6 mg oestradiol (Provames 2 mg) or a progressive dose (2 mg/day during 3 days, 4 mg/day during 5 days and then 6 mg/day) on day 1-28 combined with 400 to 800 mg per day of progesterone (Utrogestan 200 mg) from days 15-28. All patients were recruited for endometrial receptivity appreciation during the theoretical implantation window between Pg+5 to Pg+8 (Pg, progesterone) using the Win-Test (1, 24) and thawed-cryopreserved embryo replacement according to the Win-Test result.

For miRNome profiling, twenty RIF patients (mean±SEM, age: 35.9±1.4) diagnosed as non-receptive (n=5) and receptive (n=15) with the Win-test were selected.

To validate selected miRNAs candidates by quantitative RT-PCR (qRT-PCR), twenty RIF patients (mean±SEM, age: 38.3±1.2) were selected.

RNA Extraction

Total RNA were extracted from endometrial biopsies with the RNeasy Mini Kit (Qiagen, Valencia, Calif., USA) according to the manufacturer's instructions. The total RNA quantity was measured with a Nanodrop ND-1000 spectrophotometer (nanodrop Technologies Inc., DE, USA) and RNA integrity was assessed with an Agilent 2100 Bioanalyzer (Agilent, palo Alto, Calif., USA).

Microarray Hybridization and Data Analysis

Affymetrix microarrays were processed at the Microarray Core Facility of the Institute for Regenerative Medicine and Biotherapy, CHRU-INSERM-UM Montpellier (http://irmb-.chu-montpellier.fr). Total RNA (100 ng) was used to prepare labelled RNA samples for hybridization with Affymetrix® miRNA 4.1 Array Strips (Affymetrix, United Kingdom, UK). Each endometrial sample was processed individually on GeneChip miRNA array strips (4 samples/strip). Scanned GeneChip images were processed using the Affymetrix Expression Console 1.4.1 software to obtain the intensity value signal and the absent/present detection call for each probe set using the default analysis settings and global scaling as first normalization method. Probe intensities were derived using the RMA (robust multi-array analysis) algorithm.

To identify miRNAs related to the endometrial receptivity, we compared miRNA expression profiles between patients diagnosed with a non-receptive (n=5) and receptive (n=15) endometrium during the theoretical implantation window. A first selection was carried out using the detection call (Present in a least 1 endometrial sample). Then, the significant analysis of microarrays (SAM, Stanford University, USA) was used to identify miRNAs that were significantly differentially between groups. Three distinct statistical analyses (ANOVA, Student's t test and Wilcoxon signed-rank test) were used with the following criteria: fold change, FC>2; false discovery rate, FDR<5%.

Taqman miRNA Assays

Complementary DNA was synthesized from total RNA from individual endometrial biopsies using using the TaqMan miRNA-specific primers, miR-3148, miR-4423-3p, miR-455-3p (ref: #4427975, Life Technologies), according to the TaqMan MicroRNA reverse transcription kit protocol (ref: 4366597, Applied Biosystems). For reverse transcription, 250 μg of RNA sample, 0.15 μl (100 mM) dNTPs, 1 μl of 50 U/μl Multiscribe reverse transcriptase enzyme, 1.5 μl of 10× RT buffer, 0.19 μl of 20 U/μl RNase inhibitor and 3 μL of 5× RT primer (TaqMan MicroRNA Reverse Transcription Kit; Applied Biosystems) were used. Reaction mixtures (15 μl) were incubated first at 16° C. for 30 min and then at 42° C. for 30 min, inactivated at 85° C. for 5 min and then stored at 4° C. Quantitative PCR was performed using the Roche LightCycler 480. The 10 μl PCR reaction mixtures included 3 μl of RT product, 5 μl 2× TaqMan (No AmpErase UNG) Universal PCR Master Mix (ref: 4324018, Life Technologies) and 0.5 μl of primer from the 20× TaqMan MicroRNA Assays (ref: 4427975; Applied Biosystems). Reaction mixtures were incubated in a 384-well plate at 95° C. for 10 min, followed by 50 cycles at 95° C. for 15 s and at 60° C. for 60 s. MiR-16-5p were used as reference genes for normalization of the miRNA expression levels.

Statistical Analyses

Excepted for transcriptomic data, statistical analyses were performed with the GraphPadInStat 3 software. Data are expressed as the mean±SEM and differences between groups were considered significant when the Student's t-test gave a P<0.05.

Results

Endometrial miRNome Profiles Associated with Endometrial Receptivity

SAM analyses identified 11, 5 and 8 miRNAs that were differentially expressed in receptive vs non-receptive endometrium samples, using the ANOVA, Student's t-test and Wilcoxon signed-rank test, respectively. We selected 2 miRNAs (miR-3128, miR-455-3p) and 3 miRNAs (miR-4423-3p, miR-4445-3p, miR-3201) in common between three and two statistical analyses, respectively, that were all downregulated in receptive endometrial samples compared with non-receptive samples (FIG. 1).

Two candidates were validated by qRT-PCR in an independent cohort of endometrial samples (n=36) and revealed promising results (FIG. 2).

The determination with the Win-Test of the adequate time for frozen embryo transfer significantly improves pregnancy rate, whatever the day of embryo vitrification (D3 or D5/6). In addition, analysis of microRNA expression profile of receptive or non-receptive endometrium biopsies allowed us to identify microRNAs that are specifically deregulated in patients with repeated implantation failure (RIF). Importantly, our preliminary results indicate that some of these microRNAs can be detected by RT-qPCR also in blood samples (data not shown). This information will be used to develop a non-invasive diagnostic/prognostic tool to limit the use of invasive endometrial biopsies for the evaluation of endometrial receptivity.

Example 2

Material & Methods

Study Design and Sample Collection

The study group comprised 15 infertile patients (mean±SEM, age: 36.3±1.6 years) with repeated implantation failures (RIFs).

All patients were recruited after written informed consent. These patients were under hormone replacement therapy (HRT) awaiting for replacement of cryopreserved after history of RIFs (≥3) after cryopreserved embryo replacement. HRT regimen involved either a daily oral dose of 6 mg oestradiol (Provames 2 mg) or a progressive dose (2 mg/day during 3 days, 4 mg/day during 5 days and then 6 mg/day) on day 1-28 combined with 400 to 800 mg per day of progesterone (Utrogestan 200 mg) from days 15-28. All patients were recruited for endometrial receptivity appreciation during the theoretical implantation window between Pg+5 to Pg+8 (Pg, progesterone) using the Win-Test (1, 24) and thawed-cryopreserved embryo replacement according to the Win-Test result.

Then, we compared the miRNome profiles of receptive patients with positive beta-hCG (n=10) and negative beta-hCG (n=5).

RNA Extraction

Total RNA were extracted from endometrial biopsies with the RNeasy Mini Kit (Qiagen, Valencia, Calif., USA) according to the manufacturer's instructions. The total RNA quantity was measured with a Nanodrop ND-1000 spectrophotometer (nanodrop Technologies Inc., DE, USA) and RNA integrity was assessed with an Agilent 2100 Bioanalyzer (Agilent, palo Alto, Calif., USA).

Microarray Hybridization and Data Analysis

Affymetrix microarrays were processed at the Microarray Core Facility of the Institute for Regenerative Medicine and Biotherapy, CHRU-INSERM-UM Montpellier (http://irmb-.chu-montpellier.fr). Total RNA (100 ng) was used to prepare labelled RNA samples for hybridization with Affymetrix® miRNA 4.1 Array Strips (Affymetrix, United Kingdom, UK). Each endometrial sample was processed individually on GeneChip miRNA array strips (4 samples/strip). Scanned GeneChip images were processed using the Affymetrix Expression Console 1.4.1 software to obtain the intensity value signal and the absent/present detection call for each probe set using the default analysis settings and global scaling as first normalization method. Probe intensities were derived using the RMA (robust multi-array analysis) algorithm.

For the identification of miRNAs associated with implantation failure, we compared the endometrial miRNomes of receptive patients with a positive β-hCG (n=10) and receptive patients with a negative β-hCG (n=5) after personalized embryo transfer.

A first selection was carried out using the detection call (Present in a least 1 endometrial sample). Then, the significant analysis of microarrays (SAM, Stanford University, USA) was used to identify miRNAs that were significantly differentially between groups. Three distinct statistical analyses (ANOVA, Student's t test and Wilcoxon signed-rank test) were used with the following criteria: fold change, FC>2; false discovery rate, FDR<5%.

Results

Endometrial miRNome Profiles Associated with Embryo Implantation Failure

SAM analyses identified 22 and 8 miRNAs (ANOVA and Student's t-test, respectively) that were differentially expressed between receptive patients with positive or negative beta-hCG. The Wilcoxon signed-rank test failed to identify any differentially expressed small non-coding RNA in these two groups. Six small non-coding RNA identified using the ANOVA and t-test were overexpressed in endometrium samples from patients with implantation failure (Table 2).

TABLE 2

The six small non-coding RNA over-expressed in endometrium from patients with implantation failure

| Accession number | Name | Fold change | p-value |
|---|---|---|---|
| MIMAT0019073 | hsa-miR-4534 | 3.22 | 0.004675 |
| ACA15 | ACA15 | 2.55 | 0.020101 |
| ENSG00000206785 | ENSG00000206785 | 2.55 | 0.020101 |
| ENSG00000207062 | ENSG00000207062 | 2.55 | 0.020101 |
| MIMAT0000064 | hsa-let-7c-5p | 5.35 | 0.028477 |
| MIMAT0000063 | hsa-let-7b-5p | 3.56 | 0.029924 |

We selected three for future RT-qPCR validation: let-7b-5p, let-7c-5p and miR-4534.

In addition, due to the strong miRNome signature related to miscarriage (see example 3), we performed an additional sub-analysis of microarray data including only patients with a positive β-hCG and a live birth (n=5) and excluded patients a positive β-hCG and miscarriage (n=5). Initially, the positive β-hCG group (n=10) included 5 patients pregnant patients with a live birth and 5 with miscarriage. Using this sub-analysis, SAM analyses identified 240, 242 and 257 miRNAs that were differentially expressed between receptive patients with positive and negative β-hCG, using the ANOVA, Student's t-test and Wilcoxon signed-rank test, respectively. 215 miRNAs were in common to the three statistical analyses. Three have been selected for future RT-qPCR validation: miR-214-3p, miR-15b-5p, miR-424-3p.

MiRNA Quantification in Serum Samples using the TaqMan miRNA Assay:

We then quantified some of these miRNAs in serum. Blood samples were collected during the supposed implantation window concomitantly with the endometrial biopsy. Briefly, total RNA was extracted from 200 µl serum using the miRNeasy Serum/Plasma Kit (Qiagen) and miRNA expression was assessed using miR-specific TaqMan quantitative PCR primers and reagents (Life technologies). Our preliminary RT-qPCR data show that the selected miRNAs can be detected in serum samples and were well overexpressed in serum from patients with a negative β-hCG (FIG. 3), paving the way to the development of a non-invasive diagnostic/prognostic test.

Endometrial receptivity assessment is a crucial step in IVF/ICSI programs. By performing miRNA screening in receptive endometrial samples (unpublished data) diagnosed with the win-test and personalized embryo replacement, we identified miRNAs that are differentially expressed according to implantation failure. Our preliminary results confirms that these miRNAs can be detected in blood samples with the aim of developing a non-invasive diagnostic/prognostic tool to limit/avoid the use of endometrial biopsies. This approach could lead to the development of a new powerful, non-invasive clinical tool for the rapid and easy assessment for the prediction of implantation failure.

Example 3

Material & Methods

Study Design and Sample Collection

The study group comprised 10 infertile patients (mean±SEM, age: 37.3±2 years) with repeated implantation failures (RIFs).

All patients were recruited after written informed consent. These patients were under hormone replacement therapy (HRT) awaiting for replacement of cryopreserved after history of RIFs (≥3) after cryopreserved embryo replacement. HRT regimen involved either a daily oral dose of 6 mg oestradiol (Provames 2 mg) or a progressive dose (2 mg/day during 3 days, 4 mg/day during 5 days and then 6 mg/day) on day 1-28 combined with 400 to 800 mg per day of progesterone (Utrogestan 200 mg) from days 15-28. All patients were recruited for endometrial receptivity appreciation during the theoretical implantation window between Pg+5 to Pg+8 (Pg, progesterone) using the Win-Test (1, 24) and thawed-cryopreserved embryo replacement according to the Win-Test result.

Then, we compared the miRNome profiles of receptive patients with miscarriage at 8-12 weeks of amenorrhea and receptive patients with live birth.

RNA Extraction

Total RNA were extracted from endometrial biopsies with the RNeasy Mini Kit (Qiagen, Valencia, Calif., USA) according to the manufacturer's instructions. The total RNA quantity was measured with a Nanodrop ND-1000 spectrophotometer (nanodrop Technologies Inc., DE, USA) and RNA integrity was assessed with an Agilent 2100 Bioanalyzer (Agilent, palo Alto, Calif., USA).

Microarray Hybridization and Data Analysis

Affymetrix microarrays were processed at the Microarray Core Facility of the Institute for Regenerative Medicine and Biotherapy, CHRU-INSERM-UM Montpellier (http://irmb- .chu-montpellier.fr). Total RNA (100 ng) was used to prepare labelled RNA samples for hybridization with Affymetrix® miRNA 4.1 Array Strips (Affymetrix, United Kingdom, UK). Each endometrial sample was processed individually on GeneChip miRNA array strips (4 samples/strip). Scanned GeneChip images were processed using the Affymetrix Expression Console 1.4.1 software to obtain the intensity value signal and the absent/present detection call for each probe set using the default analysis settings and global scaling as first normalization method. Probe intensities were derived using the RMA (robust multi-array analysis) algorithm.

For the identification of miRNAs associated with early miscarriages, we compared the endometrial miRNomes of pregnant patients with a live birth (n=5) and with an early miscarriage (n=5).

A first selection was carried out using the detection call (Present in a least 1 endometrial sample). Then, the significant analysis of microarrays (SAM, Stanford University, USA) was used to identify miRNAs that were significantly differentially between groups. Three distinct statistical analyses (ANOVA, Student's t test and Wilcoxon signed-rank test) were used with the following criteria: fold change, FC>2; false discovery rate, FDR<5%.

Results

Endometrial miRNome Profiles Associated with Miscarriage

SAM analyses identified 146, 206 and 208 miRNAs (ANOVA, t-test and Wilcoxon signed-rank test, respectively) that were differentially expressed in endometrium samples from pregnant patients with a live birth or miscarriage. 126 of these miRNAs were identified by all three analyses and were over-expressed in endometrium samples from patients with miscarriage. Nine of them were selected for future RT-qPCR validation: miR-181a-5p, miR-574-3p, miR-92a-3p, miR-320c, let-7d-5p, miR-125a-5p, miR-320a, miR-320b, let-7f-5p (FIG. 4). Experiments are under investigations.

Endometrial receptivity assessment is a crucial step in IVF/ICSI programs. By performing miRNA screening in receptive endometrial samples (unpublished data) diagnosed with the win-test and personalized embryo replacement, we identified miRNAs that are differentially expressed according to IVF/ICSI outcomes (early embryo miscarriage, live birth). This approach could lead to the development of a new powerful, non-invasive clinical tool for the rapid and easy assessment for the prediction of early miscarriage.

REFERENCES

Throughout this application, various references describe the state of the art to which this invention pertains. The disclosures of these references are hereby incorporated by reference into the present disclosure.

1—Haouzi D, Mahmoud K, Fourar M, Bendhaou K, Dechaud H, De Vos J, Rème T, Dewailly D, Hamamah S. Identification of new biomarkers of human endometrial receptivity in the natural cycle. Hum Reprod 2009a; 24:198-205.

2—Haouzi D, Assou A, Mahmoud K, Tondeur S, Rème T, Hedon B, J. De Vos J, Hamamah S. Gene expression profile of the human endometrial receptivity: comparison between natural and stimulated cycles for the same patients. Hum Reprod 2009b; 24: 1436-1445.

3—Haouzi D, Assou S, Dechanet C, Anahory T, Dechaud H, De Vos J, Hamamah S. Controlled ovarian hyperstimulation for in vitro fertilization alters endometrial receptivity in humans: protocol effects. BiolReprod 2010; 82: 679-686.

4—Haouzi D, Dechaud H, Assou S, De Vos J, Hamamah S. Insights into human endometrial receptivity from transcriptomic and proteomic data. Reprod Biomed Online. 2012; 24(1):23-34.

5—Bissonnette L, et al. Human S100A10 plays a crucial role in the acquisition of the endometrial receptivity phenotype. Cell AdhMigr. 2016; 10(3):282-98.

6—Zhao J J, et al. Genome-wide microRNA profiling in human fetal nervous tissues by oligonucleotide microarray. Childs Nery Syst. 2006; 22(11):1419-25.

7—Zhao J J, et al. Identification of miRNAs associated with tumorigenesis of retinoblastoma by miRNA microarray analysis. Childs Nery Syst. 2009; 25(1):13-20.

8—Yao N, Lu CL, Zhao J J, Xia H F, Sun D G, Shi X Q, Wang C, Li D, Cui Y, Ma X. A network of miRNAs expressed in the ovary are regulated by FSH. Front Biosci. 2009; 14:3239-45.

9—Creighton C J, et al. Discovery of novel microRNAs in female reproductive tract using next generation sequencing. PLoS One. 2010; 5(3):e9637.

10—Bueno M J, Malumbres M. MicroRNAs and the cell cycle. BiochimBiophysActa. 2011; 1812(5):592-601.

11—Vilella F, et al. Hsa-miR-30d, secreted by the human endometrium, is taken up by the pre-implantation embryo and might modify its transcriptome. Development. 2015; 142(18):3210-21.

12—Pan Q, et al. The expression profile of micro-RNA in endometrium and endometriosis and the influence of ovarian steroids on their expression.Mol Hum Reprod. 2007; 13(11): 797-806.

13—Boren T, et al. MicroRNAs and their target messenger RNAs associated with endometrial carcinogenesis. GynecolOncol. 2008; 110(2):206-15.

14—Ohlsson Teague E M, et al. MicroRNA-regulated pathways associated with endometriosis. MolEndocrinol. 2009; 23(2):265-75.

15—Kuokkanen S, et al. Genomic profiling of microRNAs and messenger RNAs reveals hormonal regulation in microRNA expression in human endometrium. BiolReprod. 2010; 82(4):791-801.

16—Garzon R, et al. Targeting microRNAs in cancer: rationale, strategies and challenges. Nat Rev Drug Discov. 2010; 9(10):775-89.

17—Backes C, et al. Specific miRNA Disease Biomarkers in Blood, Serum and Plasma: Challenges and Prospects. MolDiagnTher.2016 Jul. 4.

The invention claimed is:

1. A method for implanting an embryo in a woman undergoing in vitro fertilization (IVF), wherein said method comprises the steps of:
 a) measuring, in an endometrial tissue sample obtained from said woman, the expression level of miR-4423-3p;
 b) determining that the woman has a receptive endometrium when:
  i) the level of miR-4423-3p is decreased in said endometrial tissue sample in comparison to the level of mi-4423-3P in control endometrial tissue samples obtained from women with non-receptive endometria, or
  ii) the level of miR-4423-3p is statistically similar to the level of mi-4423-3p in control endometrial tissue samples obtained from women with receptive endometria; and c) implanting an embryo in said woman determined to have a receptive endometrium.

2. The method according to claim 1, wherein step a) further comprises measuring an expression level of miR-455-3p, miR-4445-3p, miR-3128, and/or miR-3201.

3. The method according to claim 1, wherein step a) further comprises measuring an expression level let 7b-5p, let-7c-5p, miR-4534, miR-214-3p, miR-15b-5p and/or miR-424-3p.

4. The method according to claim 1, wherein step a) further comprises measuring an expression level of miR-181 a-5p, miR-574-3p, miR-92 a-3p, miR-320 c, let-7d-5p, miR-125 a-5p, miR-320 a, miR-320 b and/or let-7f-5p.

* * * * *